United States Patent
Park et al.

(10) Patent No.: US 11,391,653 B2
(45) Date of Patent: Jul. 19, 2022

(54) COMPOSITION FOR IMMUNOSTAINING CLEARED LARGE TISSUES AND METHOD FOR IMMUNOSTAINING CLEARED LARGE BIOLOGICAL TISSUES

(71) Applicant: Korea Research Institute of Chemical Technology, Daejeon (KR)

(72) Inventors: SunHyun Park, Daejeon (KR); Ki-Suk Kim, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 17/051,126

(22) PCT Filed: Feb. 14, 2019

(86) PCT No.: PCT/KR2019/001822
§ 371 (c)(1),
(2) Date: Oct. 27, 2020

(87) PCT Pub. No.: WO2019/208920
PCT Pub. Date: Oct. 31, 2019

(65) Prior Publication Data
US 2021/0231539 A1    Jul. 29, 2021

(30) Foreign Application Priority Data

Apr. 27, 2018    (KR) .................... 10-2018-0048947

(51) Int. Cl.
*G01N 1/30*    (2006.01)
*G01N 33/532*    (2006.01)
(Continued)

(52) U.S. Cl.
CPC ............. *G01N 1/30* (2013.01); *G01N 33/532* (2013.01); *G01N 33/577* (2013.01);
(Continued)

(58) Field of Classification Search
CPC ...... G01N 1/30; G01N 33/532; G01N 33/577; G01N 2001/302
See application file for complete search history.

(56) References Cited

U.S. PATENT DOCUMENTS

2008/0038822 A1    2/2008    Morris et al.
2009/0246824 A1    10/2009    Wiederhold et al.
(Continued)

FOREIGN PATENT DOCUMENTS

CN    104950033 A    9/2015
CN    106323708 A    1/2017
(Continued)

OTHER PUBLICATIONS

Tanigawa et al. (JP 2015-049101)—machine translation. Mar. 16, 2015.*
(Continued)

*Primary Examiner* — Gailene Gabel

(57) ABSTRACT

The present invention relates to a composition for immunostaining cleared large tissues and a method for immunostaining cleared large biological tissues using the same. The composition for immunostaining cleared large tissues increases antibody permeability in cleared biological tissues, in particular, large biological tissues having a thickness of 3 mm or more, to allow antibodies to penetrate deep into thick tissues, thereby overcoming immunostaining problems associated with limited permeation of antibodies in existing methods, reduces the time required for immunostaining large tissues, thereby enabling simple and rapid three-dimensional bioimaging with high resolution for large biological tissues, and may be beneficially used, through structure images, for identifying the causes of various diseases, developing new treatment methods, and predicting the efficacy and toxicity of drugs. Furthermore, the composition for immunostaining cleared large tissues may be used in combination with various medical devices, and in particular, may be prepared as a kit and beneficially used as an in vitro diagnostic device.

10 Claims, 3 Drawing Sheets

(51) Int. Cl.
  *G01N 33/68* (2006.01)
  *G01N 33/577* (2006.01)
(52) U.S. Cl.
  CPC ..... *G01N 33/6854* (2013.01); *G01N 33/6872* (2013.01); *G01N 2001/302* (2013.01)

(56) References Cited

U.S. PATENT DOCUMENTS

2014/0178927 A1* 6/2014 Miyawaki .......... G01N 33/5008 435/40.5
2017/0370811 A1* 12/2017 Turkevych .............. G01N 1/30
2020/0209118 A1* 7/2020 Erturk ................... G01N 1/286

FOREIGN PATENT DOCUMENTS

| CN | 106970051 A | 7/2017 |
| CN | 106990080 A | 7/2017 |
| CN | 107621462 A | 1/2018 |
| WO | 2016/108359 A1 | 7/2016 |

OTHER PUBLICATIONS

Methodology for Plant Reproductive Biology. Liu Xiangdong, et al.. South China University Press (Aug. 31, 2012), p. 11-29 translation.

"Basic principle and main steps of DAPI dyeing," Aug. 31, 2012, pp. 79-88 (English Translation).

Jia-Jie, Z., et al., "Establishment and Optimization Analysis of Two-dimensional Electrophoresis System on GIFT Tilapia Liver," Southwest China Journal of Agricultural Sciences, vol. 26, No. 5, Oct. 28, 2012, pp. 2122-2126 (English Abstract).

International Preliminary Report on Patentability received for PCT Patent Application No. PCT/KR2019/001822, dated Nov. 5, 2020, 14 pages. (8 pages of English Translation and 6 pages of Original Document).

International Search Report and Written Opinion received for PCT Patent Application No. PCT/KR2019/001822, dated May 23, 2019, 16 pages. (8 pages of English Translation and 8 pages of Original Document).

Chung et al., Structural and molecular interrogation of intact biological systems, Nature, 497(7449):332-337 (2013).

Ku et al., Multiplexed and scalable super-resolution imaging of three-dimensional protein localization in size-adjustable tissues, Nat. Biotech., 34(9):973-983 (2016).

Lee et al., Improved application of the electrophoretic tissue clearing technology, Clarity, to intact solid organs including brain, pancreas, liver, kidney, lung, and intestine, BMC Developmental Biology, 14:781 (2014).

Pan et al., Shrinkage-mediated imaging of entire organs and organisms using uDISCO, Nat. Methods., 13(10):859-867 (2016).

Zukor et al., Fluorescent Whole-Mount Method for Visualizing Three-Dimensional Relationships in Intact and Regenerating Adult Newt Spinal Cords, Developmental Dynamics, 239:3048-3057 (2010).

* cited by examiner

1% Triton X-100 in PBS

NeuN antibody in Cortex & Hippocampus

20% DMSO + 1% Triton X-100 + 50 mM Tris in DW

NeuN antibody in Cortex & Hippocampus

US 11,391,653 B2

COMPOSITION FOR IMMUNOSTAINING CLEARED LARGE TISSUES AND METHOD FOR IMMUNOSTAINING CLEARED LARGE BIOLOGICAL TISSUES

CROSS-REFERENCES TO RELATED APPLICATION

This application claims priority to PCT Application No. PCT/KR2019/001822 filed Feb. 14, 2019, entitled "COMPOSITION FOR IMMUNOSTAINING CLEARED LARGE TISSUES AND METHOD FOR IMMUNOSTAINING CLEARED LARGE BIOLOGICAL TISSUES", which patent application claims the benefit of and priority to Korean Patent Application No. 10-2018-0048947, filed Apr. 27, 2018, the entire contents of these applications are incorporated by reference herein in their entirety.

BACKGROUND OF THE INVENTION

1. Field of the Invention

The present invention relates to a composition for immunostaining cleared large tissues and a method for immunostaining cleared large biological tissues using the same.

2. Description of the Related Art

The medical diagnosis technique through x-ray has been developed to a very accurate diagnosis method with the processes of two-dimensional scanning such as CT or MRI and then reconstructing the scanned image into three-dimensional image for three-dimensional observation. A technique for realizing three-dimensional image by using not only light source but also ultrasound is actively used for diagnosis. However, most of the recent techniques have the micro resolution at the millimeter level, suggesting that they cannot satisfy the three-dimensional observation at the micro level that enables the analysis at the cell level. Thus, most of cell level analysis today depends on the traditional two-dimensional method. That is, biotissues such as biopsy or autopsy tissues are fixed with a fixative, and then embedded with paraffin or polymer. The sample is cut into sections in the thickness of several micrometers or nanometers so that light or electromagnetic wave can pass through. Then, the microstructure is analyzed by observing the transmitted image with an optical or electron microscope.

To obtain three-dimensional image by using such a micro imaging technique, a confocal microscope is needed. In that case, thickness information at the level of tens of micrometers can be obtained. Approximately, the thickness is limited by the depth at which the light source can penetrate. Most of the significant structures in biotissues are in the size of at least several hundreds of micrometers, so that only a part of the information can be obtained by the conventional method above. Therefore, in order to obtain the image of a thicker tissue, a series of sections in the thickness of tens of micrometers need to be prepared sequentially, followed by imaging with a microscope for each section and reconstructing thereof. In particular, for imaging a whole neuron in the brain tissue, there are problems in the process of tissue-cutting and re-constructing them because one neuron can stretch its axon up to a few meters.

A tissue clearing technique is a technique that can investigate the internal structure and protein distribution in tissue without damaging the tissue. Therefore, the advancement of the tissue clearing technique has been made in many ways to observe the tissue structure more deeply with overcoming the limitation of the conventional method and to approach the integral information on structure and molecules from various systems.

In the above method, a hydrogel support is penetrated into the tissue. When the concentration of the hydrogel increases, the degree of binding to the protein increases, and the structure becomes hard because a tight mesh structure is created. On the other hand, when the tissue becomes hard, it becomes difficult for the lipid to escape by surfactants, so the time required for clearing becomes longer. In addition, the method has a problem of causing air and black particle deposition on the tissue surface, or discoloring the tissue to yellow. Further, since it is possible to make only one brain clearing at a time, a lot of economic and time loss is caused. A bigger problem is that it is difficult for staining with antibodies to penetrate between polyacrylamides forming a network structure.

Recently, the present inventors developed a new method using SunHyun 3D image kit based on CHAPS+Urea. This method does not require any harmful or special techniques, equipments or know-hows that the conventional methods have for tissue clearing, and can easily clear the tissue by using a solution according to the order presented in the protocol. In addition, the method enables immunostaining of the cleared tissue with the relatively higher antibody permeability than the conventional tissue clearing method.

However, the biggest problem of the tissue clearing method using SunHyun 3D image Kit and the previous methods so far is that there is a limit to the method that enables immunostaining of the tissues larger than 1 mm using antibodies. The reason is the difficulty in diffusion and penetration of antibodies due to the solution used for clearing, the Hydrogel-hybridized form, and the thickness of the large tissue. Recently, efforts have been made to overcome the limitations of immunostaining. Representatively, a big problem was raised in the permeability of antibodies in the Hydrogel-hybridized form used in CLARITY, and in 2016, the magnified analysis of the proteome (MAP) showed an increase in antibody permeability by increasing the size by nearly four times compared to the basic tissue. However, this method has a fatal disadvantage, which is that the brightness of fluorescence is significantly reduced to $\frac{1}{64}$ compared to the conventional method, and that proteins, DNA and RNA are almost damaged and disappeared because the process of clearing proceeds by boiling the tissue above 95° C. In the case of the uDisco method developed to overcome the limitation of using organic solvents, it takes more than a month to perform immunostaining by permeating antibodies in the tissue with a size of 1 mm. However, this method is not generally applied by researchers or derived from research results, nor is it a commercialized method. However, this method has not been generally applied by researchers or derived research results, and it is also not a commercially available method. The method for immunostaining used in two-dimensional thin section samples has a limitation in the application of three-dimensional cleared large tissues. Therefore, in order to obtain three-dimensional bio images using immunostaining in cleared large tissues, it is inevitably necessary to develop an immunostaining composition and method suitable for cleared large tissues.

Related Prior Art Literatures are as Follows:

Patent reference 1: International Open-laid Gazette WO 2016/108359, Non-patent reference 1: Chung K, et al. (2013) Nature 497(7449): 332-337., Non-patent reference 2: Lee H, et al. BMC Developmental Biology 2014 14: 781., Non-patent reference 3: Taeyun Ku., et al. Nat Biotech.

2016, doi: 10.1038/nbt.3641., Non-patent reference 4: Pan C, et al. Nat Methods. (2016) 10 (13): 859-67.

SUMMARY OF THE INVENTION

It is an object of the present invention to provide a composition for immunostaining cleared large tissues.

It is another object of the present invention to provide a method for immunostaining cleared large biological tissues.

To achieve the above objects, in an aspect of the present invention, the present invention provides a composition for immunostaining cleared large biological tissues comprising an aqueous solution in which DMSO (Dimethyl Sulfoxide), Triton X-100 and a primary antibody are dissolved.

In another aspect of the present invention, the present invention provides a method for immunostaining cleared large biological tissues comprising the following steps:

treating the composition for immunostaining cleared large biological tissues to the cleared large biological tissues (step 1); and treating a secondary antibody to the cleared large biological tissues treated in step 1 (step 2).

In another aspect of the present invention, the present invention provides a kit for immunostaining cleared biological tissues comprising the composition for immunostaining.

Advantageous Effect

The composition for immunostaining cleared biological tissues comprising an aqueous solution in which DMSO (Dimethyl Sulfoxide), Triton X-100 and a primary antibody are dissolved increases antibody permeability in cleared biological tissues, in particular, large biological tissues having a thickness of 3 mm or more, to allow antibodies to penetrate deep into thick tissues, thereby overcoming immunostaining problems associated with limited permeation of antibodies in existing methods, reduces the time required for immunostaining large tissues, thereby enabling simple and rapid three-dimensional bioimaging with high resolution for large biological tissues, and may be beneficially used, through structure images, for identifying the causes of various diseases, developing new treatment methods, and predicting the efficacy and toxicity of drugs. Furthermore, the composition for immunostaining cleared large tissues may be used in combination with various medical devices, and in particular, may be prepared as a kit and beneficially used as an in vitro diagnostic device.

DESCRIPTION OF THE PREFERRED EMBODIMENTS

Figure 1:
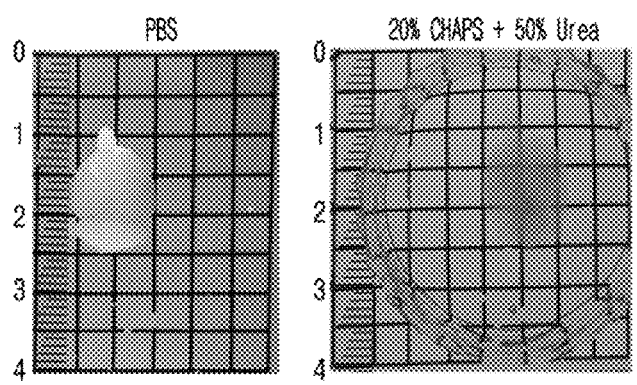
FIG. 1 a set of photographs showing the images of the cleared mouse brain prepared in Preparative Example 1.

Hereinafter, the present invention is described in detail.

It is an object of the present invention to provide a composition for immunostaining cleared large biological tissues. Particularly, It is an object of the present invention to provide a composition for immunostaining that enables clear, high-resolution three-dimensional imaging to the inside of large biological tissues with a thickness of 3 mm or more due to increased antibody permeability and improved permeability of primary antibodies.

To achieve the above objects, in an aspect of the present invention, the present invention provides a composition for immunostaining cleared biological tissues comprising an aqueous solution in which DMSO (Dimethyl Sulfoxide), Triton X-100 and a primary antibody are dissolved.

The composition can contain 5 to 50 parts by volume of DMSO, preferably 10 to 40 parts by volume of DMSO, and more preferably 20 parts by volume of DMSO based on 100 parts by volume of total composition.

If DMSO is included in less than 5 parts by volume, the primary antibody would not penetrated deeply enough into the cleared biological tissue, so that a composition for immunostaining capable of clear, high-resolution three-dimensional imaging to the inside of large biological tissues with a thickness of 3 mm or more cannot be obtained. On the other hand, if more than 50 parts by volume of DMSO is included, quenching of the primary antibody may occur, making immunostaining difficult.

The composition can contain 0.01 to 10 parts by volume of Triton X-100, preferably 0.1 to 5 parts by volume of Triton X-100, and more preferably 1 part by volume of Triton X-100 based on 100 parts by volume of total composition.

If Triton X-100 is included in less than 0.01 part by volume, there can be a problem in making a hole in the cell membrane. On the other hand, if more than 10 parts by volume of Triton X-100 is included, the size of the tissue would be too small, and thus antibody permeability would be reduced.

The composition for immunostaining cleared biological tissues can further contain Tris (tris(hydroxymethyl)aminomethane) for the purpose of preventing the excessive DMSO contained from quenching the primary antibody, but not always limited thereto.

The Tris can be further included in the composition at a concentration of 0.01 to 10% (w/v). For example, when the total composition is 100 mL, Tris can be contained by 0.01 to 10 g.

In addition, the Tris can be further included in the composition at a concentration of 0.1 to 5% (w/v), and preferably at a concentration of 1% (w/v). The Tris can prevent DMSO from quenching the primary antibody. If the Tris is included in less than 0.01% (w/v), the degeneration of the antibody may occur. On the other hand, if the Tris is included in more than 10% (w/v), there may be a problem in antibody permeability by reducing the size of the tissue.

The biological tissue can be made of cells derived from the brain, blood vessel, liver, lung, kidney, pancreas, heart and intestine separated from a living body, but not always limited thereto.

In addition, the biological tissue can be a large tissue having a thickness of 3 mm or more.

The composition can increase the antibody permeability and improve the resolution of immunostaining in the cleared large biological tissues having a thickness of 3 mm or more.

The clearing can be performed through the conventional clearing method of the tissue, and the composition of the present invention is not characterized by the clarification of the tissue itself, so the clearing method is not particularly limited.

As a result of performing immunostaining of the cleared biological tissues using the composition for immunostaining cleared biological tissues, it was confirmed that the depth of immunostaining was 3 mm or more in the cleared large biological tissues with a thickness of 3 mm or more. In addition, the immunostaining image and GFP (Green Fluorescent Protein) signal were confirmed using 5× objective lens in Microscopy Lightsheet Z.1 (see Experimental Example 1 and FIG. 3).

The above results show that the problem of antibody permeability, which is a problem of the conventional tissue clearing method, has been solved. In addition, the high-definition immunostaining images are implemented, so that the high-resolution images can be obtained.

For this reason, the composition for immunostaining cleared tissues of the present invention can be used for the discovery of markers of various diseases and the study of mechanisms using the phosphorylation activity measurement, and can be applied to various brain mapping studies.

Thus, the composition for immunostaining cleared biological tissues comprising an aqueous solution in which DMSO (Dimethyl Sulfoxide), Triton X-100 and a primary antibody are dissolved increases antibody permeability in cleared biological tissues, in particular, large biological tissues having a thickness of 3 mm or more, to allow antibodies to penetrate deep into thick tissues, thereby overcoming immunostaining problems associated with limited permeation of antibodies in existing methods, reduces the time required for immunostaining large tissues, thereby enabling simple and rapid three-dimensional bioimaging with high resolution for large biological tissues, and may be beneficially used, through structure images, for identifying the causes of various diseases, developing new treatment methods, and predicting the efficacy and toxicity of drugs. Furthermore, the composition for immunostaining cleared large tissues may be used in combination with various medical devices, and in particular, may be prepared as a kit and beneficially used as an in vitro diagnostic device.

In another aspect of the present invention, the present invention provides a method for immunostaining cleared biological tissues comprising the following steps:

treating the composition for immunostaining cleared biological tissues to the cleared biological tissues (step 1); and treating a secondary antibody to the cleared biological tissues treated in step 1 (step 2).

The method for immunostaining of the present invention uses a composition for immunostaining cleared biological tissues comprising an aqueous solution in which DMSO (Dimethyl Sulfoxide) having an effect of significantly increasing antibody permeability, Triton X-100 and a primary antibody are dissolved.

According to the conventional immunostaining technology for cleared biological tissues, it is difficult to diffuse and penetrate the antibody due to the solution used for clearing, the hydrogel-hybridized form, and the thickness of the large tissue, so it is difficult to perform immunostaining of tissues having a thickness of 1 mm or more. The present invention solves this problem, and by using the composition of the present invention, diffusion and transmission of the antibody can be facilitated even in the large biological tissues having a thickness of 3 mm or more. Therefore, since the primary antibody penetrates deeply into the inside of the biological tissue, there is an advantage of obtaining clear, high-resolution 3D images of the deep inside of the tissue when the secondary antibody is subsequently treated.

In addition, in terms of the time required for immunostaining, the conventional immunostaining technology for cleared biological tissues requires performing a pretreatment step to increase antibody permeability when immunostaining the tissue having a thickness of 1 mm or more. Even if the tissue is not thick, it is often necessary to perform a prolonged pretreatment process, and there is a problem that not only the steps of the method are added more than the present invention, but also the overall method execution time takes several months. The present invention solves this problem, and by using the composition of the present invention, immunostaining can be carried out without performing any pretreatment steps and the immunostaining time of the large tissue having a thickness of 3 mm or more can be significantly shortened compared to the prior art, so there is an advantage of obtaining clear, high-resolution 3D images of the deep inside of the tissue. That is, the method of the present invention does not require any pretreatment, and by using the composition of the present invention, there is an advantage that the antibody permeability can be increased simply and easily.

Hereinafter, the method for immunostaining is described in detail.

Step 1 of the method for immunostaining is a step of infiltrating the primary antibody into the biological tissue by immersing the biological tissue in a composition for immunostaining cleared biological tissues comprising an aqueous solution in which DMSO (Dimethyl Sulfoxide) having an effect of significantly increasing antibody permeability, Triton X-100 and a primary antibody are dissolved.

Particularly, the composition can contain 5 to 50 parts by volume of DMSO, preferably 10 to 40 parts by volume of DMSO, and more preferably 20 parts by volume of DMSO based on 100 parts by volume of total composition.

If DMSO is included in less than 5 parts by volume, the primary antibody would not penetrated deeply enough into the cleared biological tissue, so that a composition for immunostaining capable of clear, high-resolution three-dimensional imaging to the inside of large biological tissues with a thickness of 3 mm or more cannot be obtained. On the other hand, if more than 50 parts by volume of DMSO is included, quenching of the primary antibody may occur, making immunostaining difficult.

The composition can contain 0.01 to 10 parts by volume of Triton X-100, preferably 0.1 to 5 parts by volume of Triton X-100, and more preferably 1 part by volume of Triton X-100 based on 100 parts by volume of total composition.

If Triton X-100 is included in less than 0.01 part by volume, there can be a problem in making a hole in the cell membrane. On the other hand, if more than 10 parts by volume of Triton X-100 is included, the size of the tissue would be too small, and thus antibody permeability would be reduced.

The composition can further include Tris (tris(hydroxymethyl)aminomethane).

Accordingly, the method for immunostaining of the present invention can perform step 2 by smoothly performing step 1, and enables clear, high-resolution three-dimensional imaging to the inside of large biological tissues with a thickness of 3 mm or more only when the composition for immunostaining cleared biological tissues containing DMSO and Triton X-100 in the above range is used.

In step 1, the composition for immunostaining cleared biological tissues can further contain Tris (tris(hydroxymethyl)aminomethane) for the purpose of preventing the excessive DMSO contained from quenching the primary antibody, but not always limited thereto.

The Tris can be further included in the composition at a concentration of 0.01 to 10% (w/v). For example, when the total composition is 100 mL, Tris can be contained by 0.01 to 10 g.

In addition, the Tris can be further included in the composition at a concentration of 0.1 to 5% (w/v), and preferably at a concentration of 1% (w/v). The Tris can prevent DMSO from quenching the primary antibody. If the Tris is included in less than 0.01% (w/v), the degeneration of the antibody may occur. On the other hand, if the Tris is included in more than 10% (w/v), there may be a problem in antibody permeability by reducing the size of the tissue.

In addition, in step 1, the clearing of the biological tissue can be performed through the conventional tissue clearing, and the method of the present invention is not characterized by the clearing the tissue itself, so the clearing method is not particularly limited.

Step 2 of the method for immunostaining is a step of treating the secondary antibody to the biological tissue in which the primary antibody has penetrated the tissue due to the execution of Step 1.

The method for immunostaining of the present invention is characterized in step 1, so the step of treating the secondary antibody is not limited to a specific method, and the step can be performed by the conventional method used by a person skilled in the art.

The biological tissue can be made of cells derived from the brain, blood vessel, liver, lung, kidney, pancreas, heart and intestine separated from a living body, but not always limited thereto.

In addition, the biological tissue can be a large tissue having a thickness of 3 mm or more.

The composition can increase the antibody permeability and improve the resolution of immunostaining in the cleared large biological tissues having a thickness of 3 mm or more.

As a result of performing immunostaining of the cleared biological tissues using the method for immunostaining cleared biological tissues, it was confirmed that the depth of immunostaining was 3 mm or more in the cleared large biological tissues with a thickness of 3 mm or more. In addition, the immunostaining image and GFP (Green Fluorescent Protein) signal were confirmed using 5× objective lens in Microscopy Lightsheet Z.1 (see Experimental Example 1 and FIG. 3).

The above results show that the problem of antibody permeability, which is a problem of the conventional tissue clearing method, has been solved. In addition, the high-definition immunostaining images are implemented, so that the high-resolution images can be obtained.

For this reason, the method for immunostaining of the present invention can be used for the discovery of markers of various diseases and the study of mechanisms using the phosphorylation activity measurement, and can be applied to various brain mapping studies.

Thus, the composition for immunostaining cleared biological tissues comprising an aqueous solution in which DMSO (Dimethyl Sulfoxide), Triton X-100 and a primary antibody are dissolved increases antibody permeability in cleared biological tissues, in particular, large biological tissues having a thickness of 3 mm or more, to allow antibodies to penetrate deep into thick tissues, thereby overcoming immunostaining problems associated with limited permeation of antibodies in existing methods, reduces the time required for immunostaining large tissues, thereby enabling simple and rapid three-dimensional bioimaging with high resolution for large biological tissues, and may be beneficially used, through structure images, for identifying the causes of various diseases, developing new treatment methods, and predicting the efficacy and toxicity of drugs.

Furthermore, the composition for immunostaining cleared large tissues may be used in combination with various medical devices, and in particular, may be prepared as a kit and beneficially used as an in vitro diagnostic device.

In another aspect of the present invention, the present invention provides a kit for immunostaining cleared biological tissues comprising the composition for immunostaining.

Hereinafter, the present invention will be described in detail by the following examples and experimental examples.

However, the following examples and experimental examples are only for illustrating the present invention, and the contents of the present invention are not limited thereto.

PREPARATIVE EXAMPLE 1

Preparation of Cleared Biological Tissues

The cleared biological tissue was prepared by the following method. All the animal tests described in this statement were performed according to the guidance (Approval No. RS17003) of Committee for Animal Resources, Korea Institute of Toxicology.

Particularly, adult mice (8 weeks old) were anesthetized with isoflurane (1 cc/min), an inhalation anesthetic. To stain the mouse blood vessels, Lectin-488 (Cat #DL1174) was injected through the tail vein. 5 minutes after the injection of lectin, 50 mL of ice cold 1× PBS (phosphate-buffered saline) was perfused, and then ice cold PBS containing 4% PFA was perfused again. Organs were extracted and dipped in 4% paraformaldehyde and PFA solution, followed by incubation at 4° C. for 12 hours. At this time, the temperature for ice cold condition is not limited but preferably −20° C.~−40° C.

Next, the sample was washed twice with 50 ml of PBS. The fixed sample was incubated for 3 days at 220 rpm at 37° C. in a PBS mixture solution of CHAPS (20% w/v %) and urea (60 w/v %).

The brain sample was transferred from the mixture of CHAPS and urea to tertiary distilled water, and washed three times with 50 ml of tertiary distilled water for 12 hours. After transferring the brain sample to a mixture of CHAPS and urea, a mounting solution, the brain was observed to be cleared, and the results are shown in FIG. 1.

FIG. 1 a set of photographs showing the images of the cleared mouse brain prepared in Preparative Example 1.

As shown in FIG. 1, it was confirmed that the mouse brain tissue was well-cleared.

EXAMPLE 1

Immunostaining of Biological Tissue Using Composition for Immunostaining Cleared Biological Tissues Using the composition for immunostaining cleared biological tissues of the present invention, the cleared tissue prepared in Preparative Example 1 was immunostained by the following method.

Step 1: Preparation of a Composition for Immunostaining Cleared Biological Tissues A composition for immunostaining cleared biological tissues was prepared by treating NeuN (Cat #ab177487), a neuron marker antibody, as a primary antibody to a composition consisting of 20% (v/v) DMSO, 1% (v/v) Triton X-100, 50 mM Tris and distilled water (20 mL of DMSO, 79 mL of distilled water, 1 mL of Triton X-100 and 0.65 g of Tris) at a ratio of 1:100.

Step 2: Treatment of the Composition for Immunostaining Cleared Biological Tissues (Treatment of a Primary Antibody)

The cleared tissue obtained in Preparative Example 1 was incubated for 12 hours by replacing 3 times with 50 mL of distilled water. The tissue sample was immersed in the composition obtained in step 1 and treated with the primary antibody. After treatment with the primary antibody, the tissue sample was incubated at 4° C. for 7 days.

Step 3: Treatment of a Secondary Antibody

After treatment with the primary antibody in step 2, the tissue sample was washed again with distilled water for 12 hours. The tissue sample was treated with an aqueous solution containing PBS (phosphate buffered saline), 0.1% TritonX-100, DAPI (Cat #D5942 Sigma), and Donkey Anti-rabbit IgG Alexa Fluor-647 as a secondary antibody, followed by incubation for 7 days while shaking at 4° C. After 7 days, in order to remove the non-specific antibody binding in the sample, the tissue sample was washed with an aqueous solution containing PBS and 0.1% TritonX-100 for 12 to 24 hours while shaking at 4° C. The washed sample was put in a mixed solution of CHAPS and urea, a mounting solution, followed by incubation for 12 hours. At this time, the DAPI-treated group is a chemical staining group, which is a comparative group for comparing antibody permeability between immunostaining and chemical staining.

COMPARATIVE EXAMPLE 1

Immunostaining of Biological Tissue Using TritonX-100

The cleared biological tissue prepared in Preparative Example 1 was immunostained using TritonX-100 by the following method.

The biological tissue was immunostained in the same manner as described in Example 1, except that PBS containing 1% TritonX-100 was used instead of a composition consisting of 20% DMSO, 1% Triton X-100, 50 mM Tris and distilled water.

EXPERIMENTAL EXAMPLE 1

Confirmation of Fluorescence of Immunostained Biological Tissue

To confirm the fluorescence of the immunostained biological tissues prepared in Example 1 and Comparative Example 1, the immunostaining fluorescence signals of DAPI and NeuN antibody used as neuron markers in the mouse brain were observed using 5× objective lens in Microscopy Lightsheet Z.1. The immunostained tissues using DAPI (Cat #D5942 Sigma) (chemical staining) are shown in FIG. 2, and the immunostained tissues using Donkey Anti-rabbit IgG Alexa Fluor-647 (antibody staining) are shown in FIG. 3.

Figure 2:
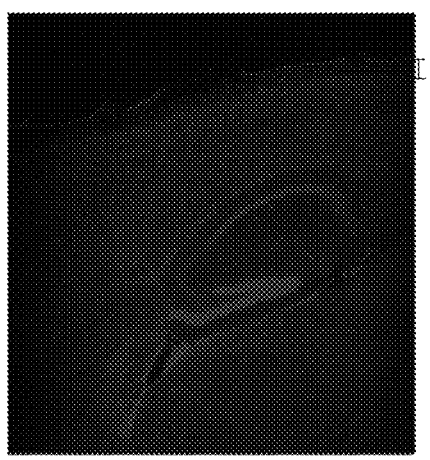
FIG. 2 is a set of photographs showing the images of the cleared brain tissue wherein DNA was stained with DAPI (4',6-diamidino-2-phenylindole).
Figure 2:
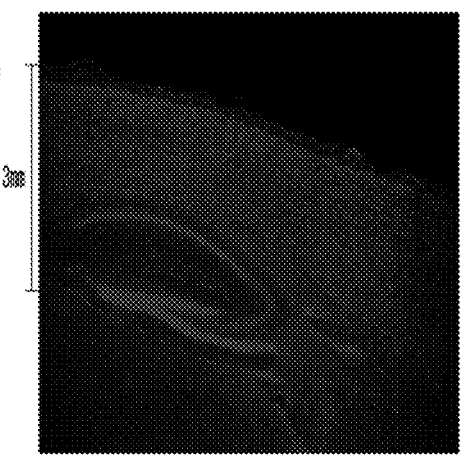

FIG. 2 is a set of photographs showing the images of the cleared brain tissue wherein DNA was stained with DAPI (4',6-diamidino-2-phenylindole).

As shown in FIG. 2, In the case of chemical staining with DAPI, it was confirmed that there was no significant difference between the two compositions.

Figure 3:
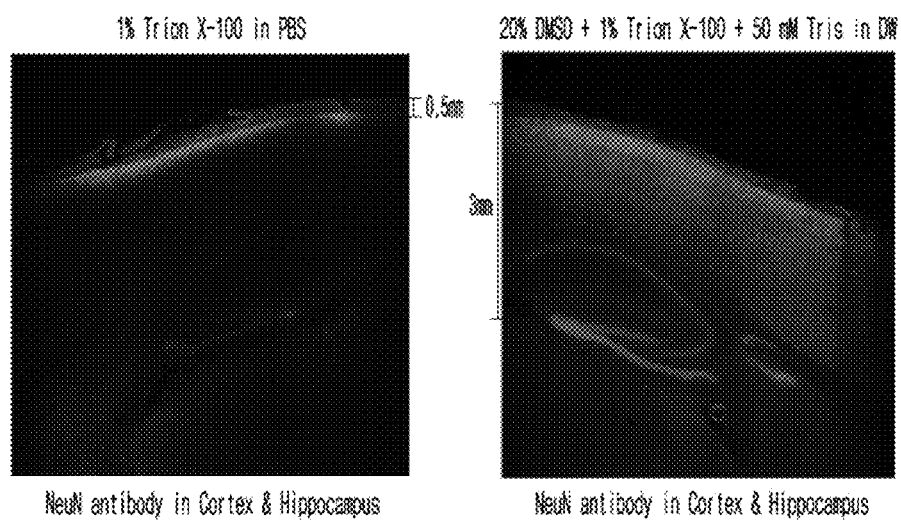
FIG. 3 is a set of photographs showing the staining images of the results of immunostaining performed using NeuN, a neuronal nuclear staining antibody used as a marker for neurons, as the primary antibody and Donkey Anti-rabbit IgG Alexa Fluor-647 as the secondary antibody with 5× objective lens in Microscopy Lightsheet Z.1.

FIG. 3 is a set of photographs showing the staining images of the results of immunostaining performed using NeuN, a neuronal nuclear staining antibody used as a marker for neurons, as the primary antibody and Donkey Anti-rabbit IgG Alexa Fluor-647 as the secondary antibody with 5× objective lens in Microscopy Lightsheet Z.1.

As shown in FIG. 3, in the case of antibody staining with Donkey Anti-rabbit IgG Alexa Fluor-647, it was confirmed that the sample immersed in the composition of Comparative Example 1 (composition consisting of 1% TritonX-100 and 1×PBS) was immunostained at a depth of 0.5 mm, but the sample immersed in the composition of Example 1 (composition of 20% DMSO, 1% Triton X-100 and 50 mM Tris in distilled water), the composition for immunostaining cleared biological tissues of the present invention was immunostained at depth of 3 mm or more.

The above results show that the problem of antibody permeability, which is a problem of the conventional tissue clearing methods, has been solved. In addition, immunostaining images are implemented in high quality, showing that high-resolution images can be obtained.

In addition, in FIG. 3, the immunostaining images and the GFP (Green Fluorescent Protein) signals were confirmed using 5× objective lens in Microscopy Lightsheet Z.1. Therefore, the composition for immunostaining cleared tissues of the present invention can be used for the discovery of markers of various diseases and the study of mechanisms using the phosphorylation activity measurement, and can be applied to various brain mapping studies.

Thus, the composition for immunostaining cleared biological tissues comprising an aqueous solution in which DMSO (Dimethyl Sulfoxide), Triton X-100 and a primary antibody are dissolved increases antibody permeability in cleared biological tissues, in particular, large biological tissues having a thickness of 3 mm or more, to allow antibodies to penetrate deep into thick tissues, thereby overcoming immunostaining problems associated with limited permeation of antibodies in existing methods, reduces the time required for immunostaining large tissues, thereby enabling simple and rapid three-dimensional bioimaging with high resolution for large biological tissues, and may be beneficially used, through structure images, for identifying the causes of various diseases, developing new treatment methods, and predicting the efficacy and toxicity of drugs. Furthermore, the composition for immunostaining cleared large tissues may be used in combination with various medical devices, and in particular, may be prepared as a kit and beneficially used as an in vitro diagnostic device.

INDUSTRIAL APPLICABILITY

The composition for immunostaining cleared large tissues of the present invention and the method for immunostaining cleared large biological tissues using the same enable three-dimensional bioimaging with high resolution for large biological tissues, and may be beneficially used, through structure images, for identifying the causes of various diseases, developing new treatment methods, and predicting the efficacy and toxicity of drugs. Furthermore, the composition of the present invention may be used in combination with various medical devices, and in particular, may be prepared as a kit and beneficially used as an in vitro diagnostic device.

What is claimed is:

1. A method for immunostaining a cleared biological tissue, the method comprising:
   (i) clearing an ex vivo biological tissue having a thickness of 1 mm to 3 mm by contacting the ex vivo biological tissue with a clearing composition comprising a mixture of 3-[(3-cholamidopropyl)dimethylammonio]-1-propanesulfonate (CHAPS) and urea to produce a cleared biological tissue having a thickness of 1 mm to 3 mm;
   (ii) applying an immunostaining composition to the cleared biological tissue to produce a permeable, cleared biological tissue, the permeable, cleared biological tissue having a thickness of 1 mm to 3 mm, the immunostaining composition comprising dimethyl sulfoxide (DMSO), polyethylene glycol tert-octylphenyl ether, and a primary antibody, the primary antibody penetrating into the permeable, cleared biological tissue; and
   (iii) applying a secondary antibody comprising a fluorescent material to the permeable, cleared biological tissue.

2. The method according to claim 1, wherein the immunostaining composition contains 5 to 50 parts by volume of DMSO based on 100 parts by volume of total composition.

3. The method according to claim 1, wherein the immunostaining composition contains 0.01 to 10 parts by volume of polyethylene glycol tert-octylphenyl ether based on 100 parts by volume of total composition.

4. The method according to claim 1, wherein the immunostaining composition further contains tris(hydroxymethyl)aminomethane (tris).

5. The method according to claim 4, wherein the immunostaining composition further contains tris at an amount of 0.01 to 10% (w/v).

6. The method according to claim 4, wherein the tris prevents DMSO from quenching the primary antibody.

7. The method according to claim 1, wherein the ex vivo biological tissue is derived from the brain, blood vessel, liver, lung, kidney, pancreas, heart or intestine.

8. The method according to claim 1, wherein the immunostaining composition increases the antibody permeability and improves the resolution of immunostaining in the cleared biological tissue.

9. The method according to claim 1, wherein the method enables three-dimensional imaging of the cleared biological tissue.

10. A kit for immunostaining cleared biological tissues comprising:
    an extracted biological tissue clearing composition comprising a mixture of 3-[(3-cholamidopropyl)dimethylammonio]-1-propanesulfonate (CHAPS) and urea; and
    an immunostaining composition comprising dimethyl sulfoxide (DMSO), polyethylene glycol tert-octylphenyl ether, and a primary antibody; and, optionally,
    a secondary antibody comprising a fluorescent material.

* * * * *